United States Patent [19]

Forman et al.

[11] 4,073,688
[45] Feb. 14, 1978

[54] PROCESS FOR THE PREPARATION OF A PROTEINACEOUS CONCENTRATE

[75] Inventors: Ladislav Forman; Milos Mergl; Jiri Mostecky; Milos Teply; Jiri Uher, all of Prague, Czechoslovakia

[73] Assignee: Vysoka skola chemicko-technologicka, Prague, Czechoslovakia

[21] Appl. No.: 644,918

[22] Filed: Dec. 29, 1975

[51] Int. Cl.² ............... C12C 11/00; C12C 11/12; C12B 1/00

[52] U.S. Cl. ............................ 195/49; 195/13; 195/31 R; 426/42; 426/41

[58] Field of Search .......... 195/29, 31 R, 49, 13, 195/123, 27, 4, 7; 426/34, 41, 39, 42, 43, 60, 13; 260/112 R

[56] References Cited

U.S. PATENT DOCUMENTS

| 2,809,113 | 10/1957 | Stimpson et al. | 426/41 |
| 3,818,109 | 6/1974 | Bechtle | 426/41 |
| 3,929,578 | 12/1975 | Urakami | 195/49 |

Primary Examiner—Raymond N. Jones
Assistant Examiner—Thomas G. Wiseman

[57] ABSTRACT

A process for the preparation of a proteinaceous concentrate by the aerobic cultivation of yeast on whey is described. The described technique involves preparing and fermenting a concentrated nutrient medium. Following fermentation, the medium is brought to a boil, cooled and again fermented with yeast in an ethyl alcohol medium.

4 Claims, No Drawings

PROCESS FOR THE PREPARATION OF A PROTEINACEOUS CONCENTRATE

BACKGROUND OF THE INVENTION

The invention relates to a process for the preparation of a proteinaceous concentrate. More particularly, the present invention relates to a process for the preparation of protein concentrates by the aerobic cultivation of yeast on whey.

In the synthesis of microbial products, it has been conventional to utilize a nutrient medium comprising whey (the serum or watery part of milk), the dry matter content of which is typically 14% protein and 70% milk sugar. In light of its composition, whey is considered to be one of the most suitable nutrient media for obtaining biomass by fermentation.

To this end, it has been common to employ various continuous fermentation techniques wherein whey is fermented by use of yeast to yield a protein-rich product. Such processes typically involve (a) the enrichment of protein-poor whey with nitrogenous substances such as urea or ammonium salts, (b) the adjustment of pH with phosphoric acid, and (c) the addition of mineral constituents such as zinc or magnesium. The resultant nutrient medium is then fermented in the presence of oxygen until the lactose content is reduced to less than 1%, thereby yielding a product which typically evidences a dry matter content ranging from 4.0–4.5% and approximately 25 grams of dry yeast per liter. The product so prepared may then be densified or, in the alternative, dried.

Although such processes have been widely used in commercial applications, economic considerations have prompted workers in the art to seek out suitable alternatives. Additional limitations also obtain in the relatively low concentration of nutrients in whey prepared in the foregoing manner.

DESCRIPTION OF THE INVENTION

In accordance with the present invention, such prior art limitations have been either obviated or substantially lessened by a novel technique for the aerobic cultivation of yeast on whey. Briefly, the inventive technique involves preparing a nutrient medium that comprises the following groups:

(1) (a) sweet whey,
  (b) acid whey, or
  (c) sweet whey fermented by lactic fermentation bacteria of the genus STREPTOCOCCUS or LACTOBACILLUS at a temperature ranging from 18°–50° C under anaerobic conditions to yield a maximum lactic acid content of 1.6% by weight;
  and
(2) mineral substances, the pH value of the medium being adjusted by the addition of an acid.

The resulting medium is permitted to ferment in the presence of oxygen. Following fermentation, the resultant product is heated to a boil to obtain coagulation of foam-forming substances. Then, the whey is cooled to a temperature ranging from 26°–34° C, and the pH is adjusted to a value ranging from 4.0–6.0 by the addition of calcium carbonate.

Following such treatment, additional fermentation is effected with yeast of the genus CANDIDA in a 0.1–0.2% by weight ethyl alcohol medium. The fermentation continues until the alcohol is consumed.

Finally, the fermented medium is densified to a pasty, pulverulent consistency.

The prime advantage of the described process resides in the use of ethanol as a carbon source in the nutrient medium, thereby permitting the attainment of significant economic savings. Additionally, the combination of nutrients in the fermented medium permits the production of a product of high biological value.

For illustration purposes, an example of the process of the invention is herewith presented without in any way limiting the generality of the foregoing:

EXAMPLE

1000 Liters of acid whey obtained as a by-product in the preparation of cottage cheese, acidified in a fermentation process to a pH of about 5, was fermented after being subjected to a treatment which included deproteinization with yeast of the genus CANDIDA and admixture with a nitrogen source and mineral materials to yield the following amounts of nutrients per 1 kg of the yeast dry content:

80 g of potassium dihydrogen phosphate;
25 g of magnesium sulfate;
1 g of zinc sulfate.

Under aerobic conditions, ethanol was added to this medium in an amount sufficient to yield a concentration of from 0.1–2.0% by weight. The pH was maintained at a value less than 6.4 by covering the yeast culture with liquid ammonia additives. Fermentation was terminated after the dry yeast content attained a value of from 3–5% corresponding with a total of 6–10% by weight of dry content of the medium. The final product was obtained by densifying the fermentation medium.

In the foregoing, an illustrative sequence of steps and materials of the inventive process has been described. Many variations and modifications will now occur to those skilled in the art. It is accordingly desired that the scope of the appended claims not be limited to the specific disclosure herein contained.

What is claimed is:

1. In a process for the preparation of a proteinaceous concentrate by aerobic activation of yeast wherein a protein-poor whey selected from the group consisting of sweet whey and acid whey is enriched with nitrogenous substances, the pH of the enriched whey is adjusted with an acid, mineral constituents are added to the whey and fermentation thereof is effected in the presence of oxygen, the improvement which comprises, subsequent to the fermentation step, heating the whey to a boil to effect coagulation of foam-forming substances, cooling the whey to a temperature within the range of 26°–34° C, adjusting the pH of the resultant solution to a value within the range of 4.0–6.0 and subjecting said solution to a second fermentation with yeast of the genus CANDIDA in an alcoholic medium, the concentration of which is maintained within the range of from 0.1–0.2%, by weight, ethanol, based on the weight of said medium, under aerobic conditions.

2. A process as defined in claim 1, wherein the protein-poor whey is sweet whey.

3. A process as defined in claim 1, wherein the pH adjusting step is effected with calcium carbonate.

4. A process as defined in claim 2, wherein the fermentation step preceding the boiling step is effected by lactic fermentation bacteria under anaerobic conditions to a maximum lactic acid content of 1.6% by weight.

* * * * *